United States Patent [19]
Teirstein et al.

[11] Patent Number: 5,234,407
[45] Date of Patent: Aug. 10, 1993

[54] METHOD AND DEVICE FOR EXCHANGING CARDIOVASCULAR GUIDE CATHETER WHILE A PREVIOUSLY INSERTED ANGIOPLASTY GUIDE WIRE REMAINS IN PLACE

[75] Inventors: Paul S. Teirstein, La Jolla; Henry Nita, Lake Forest; Jagdish C. Dhuwalia, Irvine; Scott Evans, Tustin, all of Calif.

[73] Assignee: Baxter International Inc., Deerfield, Ill.

[21] Appl. No.: 665,513

[22] Filed: Mar. 6, 1991

[51] Int. Cl.⁵ .......................................... A61M 31/00
[52] U.S. Cl. ..................................... 604/53; 604/164; 128/657; 128/772
[58] Field of Search ................ 604/53, 43, 96, 101, 604/102, 160, 164; 606/191, 192, 194, 195; 128/772, 657

[56] References Cited
U.S. PATENT DOCUMENTS

| | | | |
|---|---|---|---|
| 3,416,513 | 12/1968 | Edwards | 128/772 |
| 4,661,094 | 4/1987 | Simpson | 604/53 |
| 4,748,982 | 6/1988 | Horzewski et al. | 604/102 |
| 4,827,941 | 5/1989 | Taylor et al. | |
| 4,917,103 | 4/1990 | Gambale et al. | |
| 4,927,413 | 5/1990 | Hess | |
| 4,932,413 | 6/1990 | Shockey et al. | 604/280 |
| 4,988,356 | 1/1991 | Crittenden et al. | 604/194 |
| 5,040,548 | 8/1991 | Yock | 128/898 |

FOREIGN PATENT DOCUMENTS

| | | |
|---|---|---|
| 0232994 | 8/1987 | European Pat. Off. ............ 604/53 |
| 0388112A3 | 3/1990 | European Pat. Off. . |
| 0441384A2 | 2/1991 | European Pat. Off. . |
| 2180454A | 6/1992 | United Kingdom . |

OTHER PUBLICATIONS

"Technique for Guiding Catheter Exchange During Coronary Angioplasty While Maintaining Guidewire Access Across a Coronary Stenosis" Newton, Lewis, Vetrovee *Catheterization & Cardiovascular Diagnosis;* 15:173–175 (1988).

"Guiding Catheter Exchange During Coronary Angioplasty", Warren, Barnett; *Catherization and Cardiovascular Diagnosis;* 20:212–215 (1990).

*Primary Examiner*—Cary E. O'Connor
*Attorney, Agent, or Firm*—Robert D. Buyan

[57] ABSTRACT

A method and device for removing a first guide catheter and replacing the first guide catheter with a second guide catheter, without disturbing the placement of a flexible guide wire which has previously been inserted through the first guide catheter. The device of the invention comprises an "exchange catheter" which may be advanced over the outer surface of the pre-positioned guide wire to provide support and shielding of the guide wire during the catheter exchange procedure. A guide wire exit aperture formed in the "exchange catheter" permits the guide wire to exit the exchange catheter at a location whereby the operator may hold and manipulate the guide wire to maintain its desired position during the catheter exchange procedure.

53 Claims, 8 Drawing Sheets

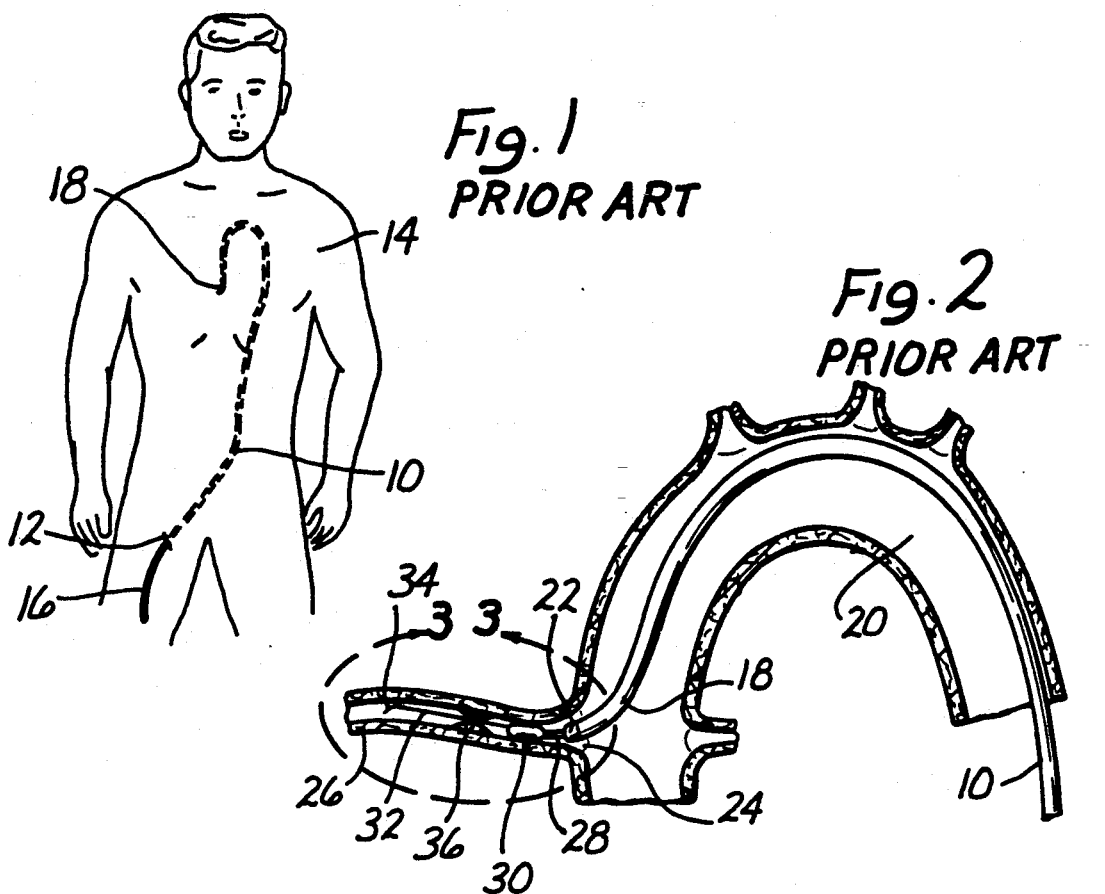
Fig. 1 PRIOR ART
Fig. 2 PRIOR ART
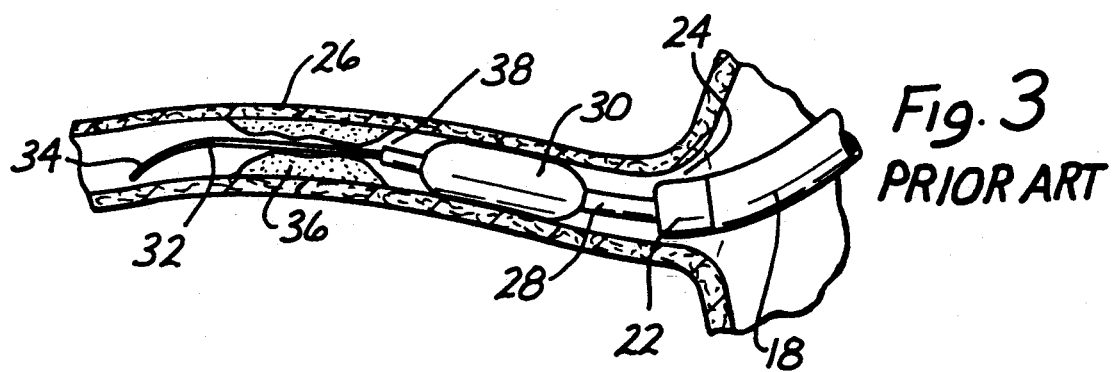
Fig. 3 PRIOR ART
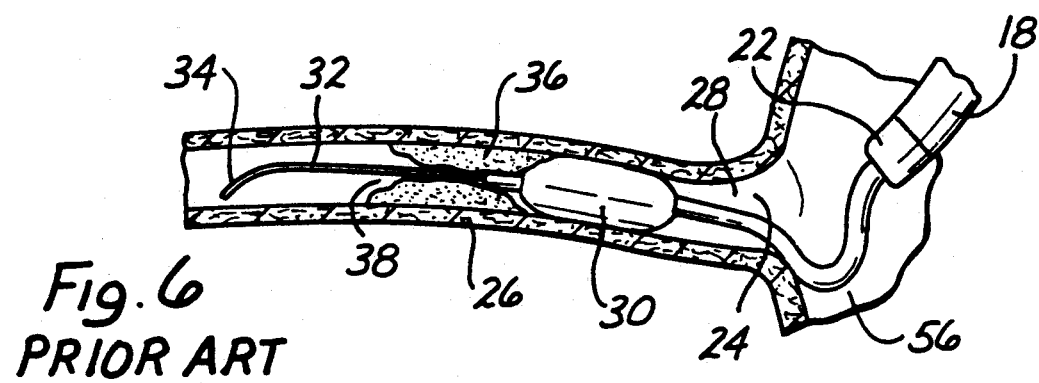
Fig. 6 PRIOR ART

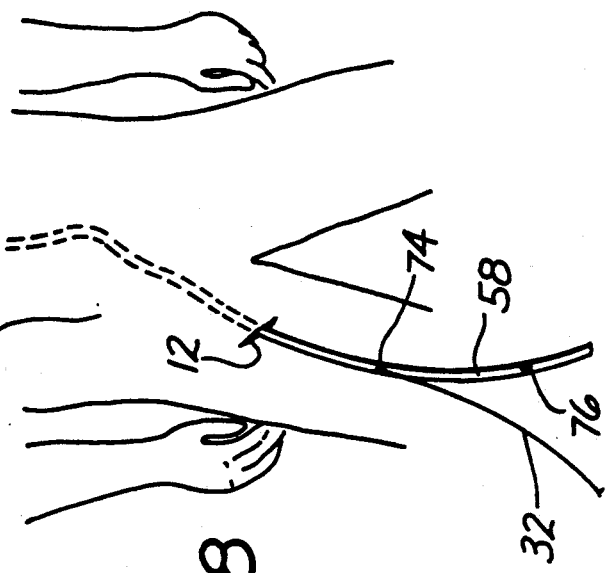
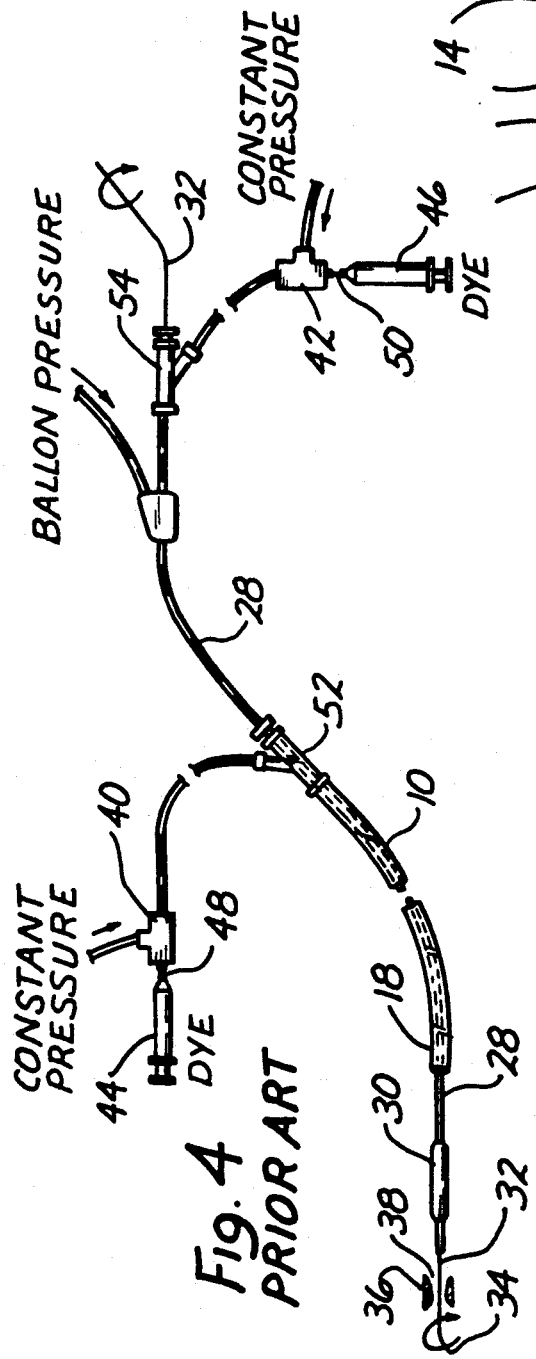
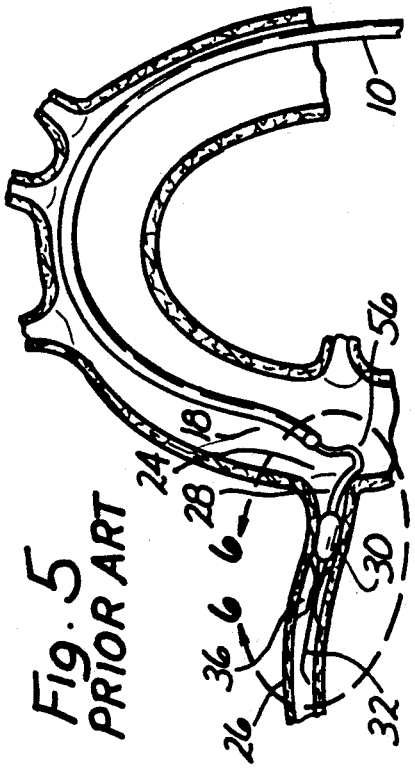

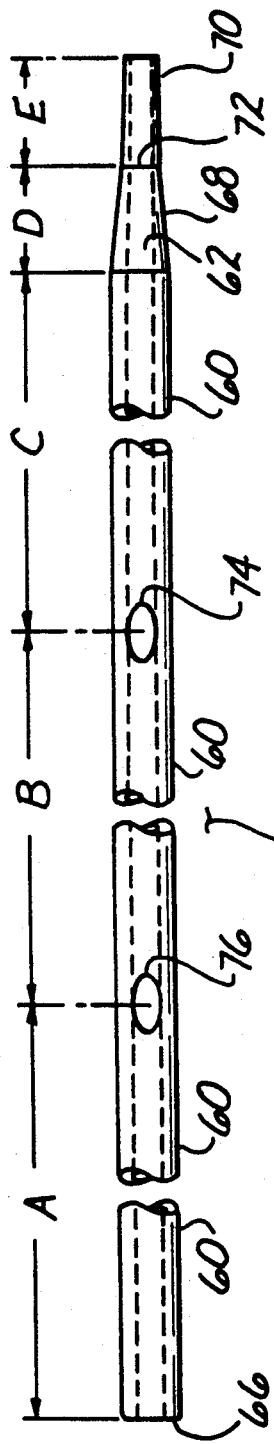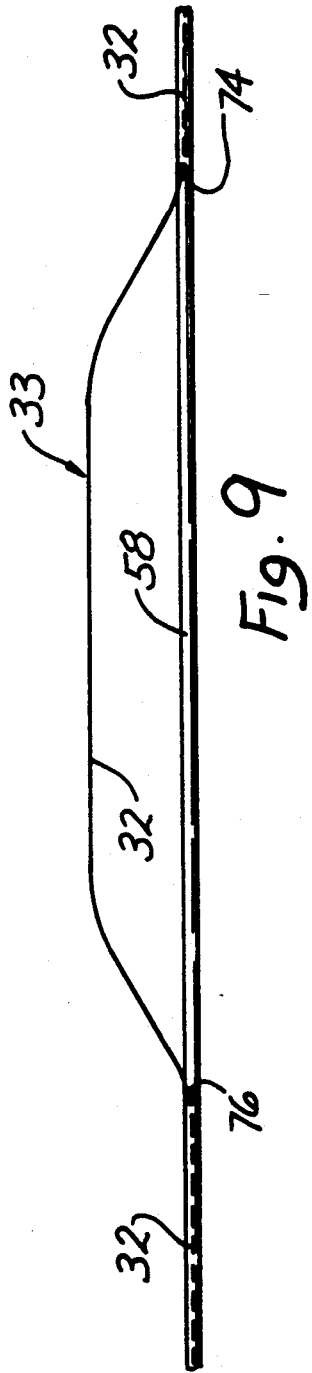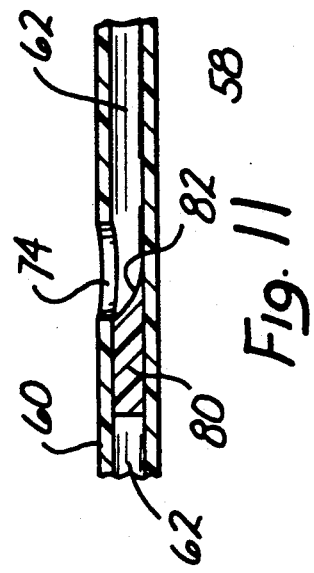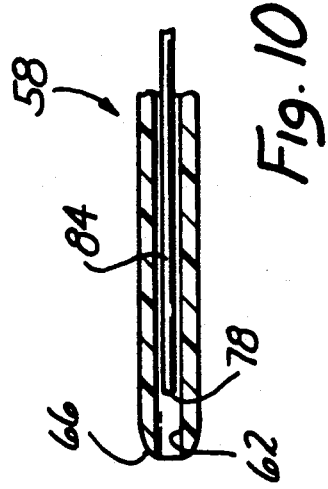

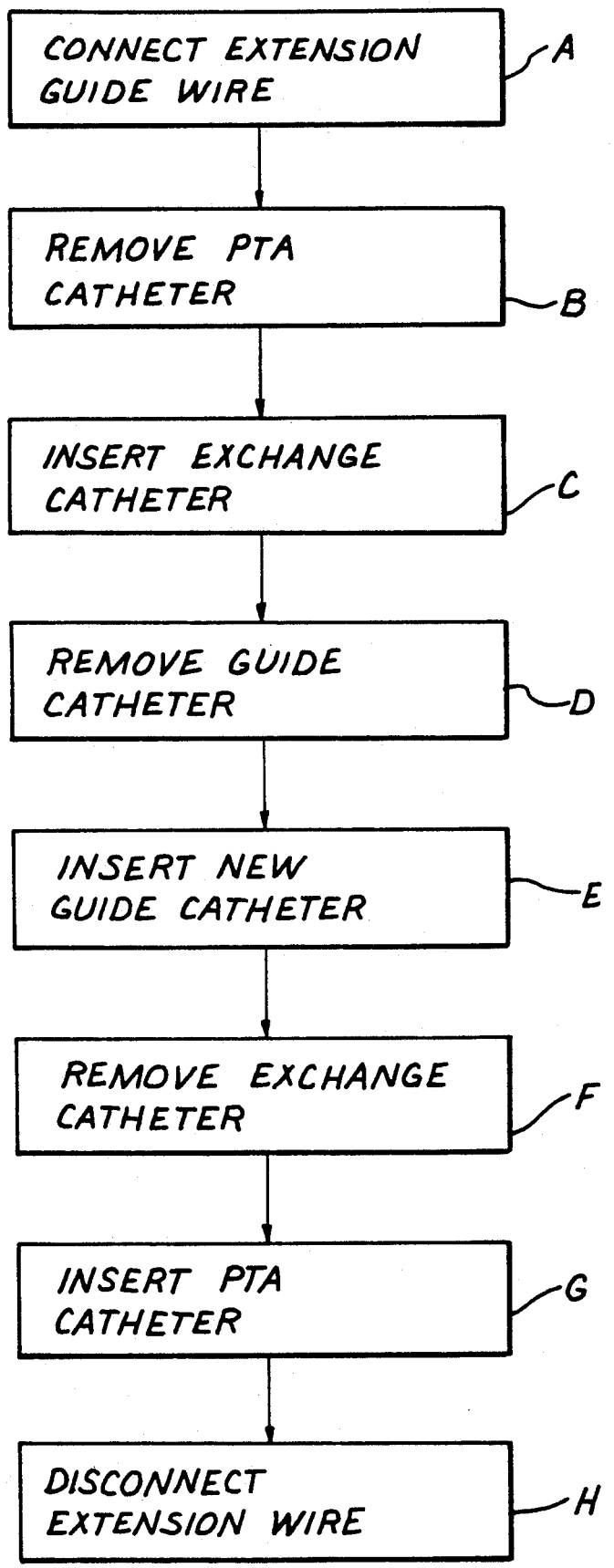

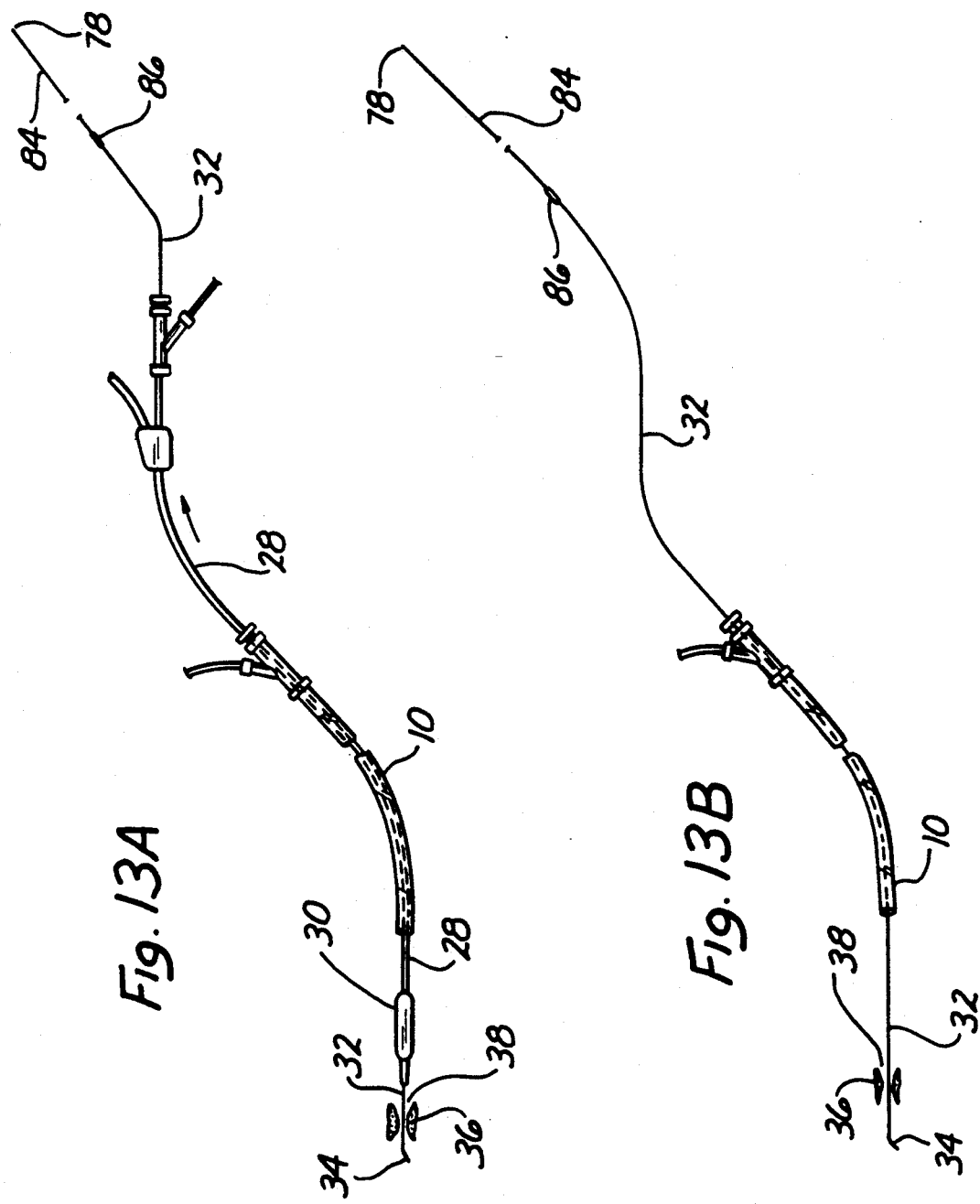

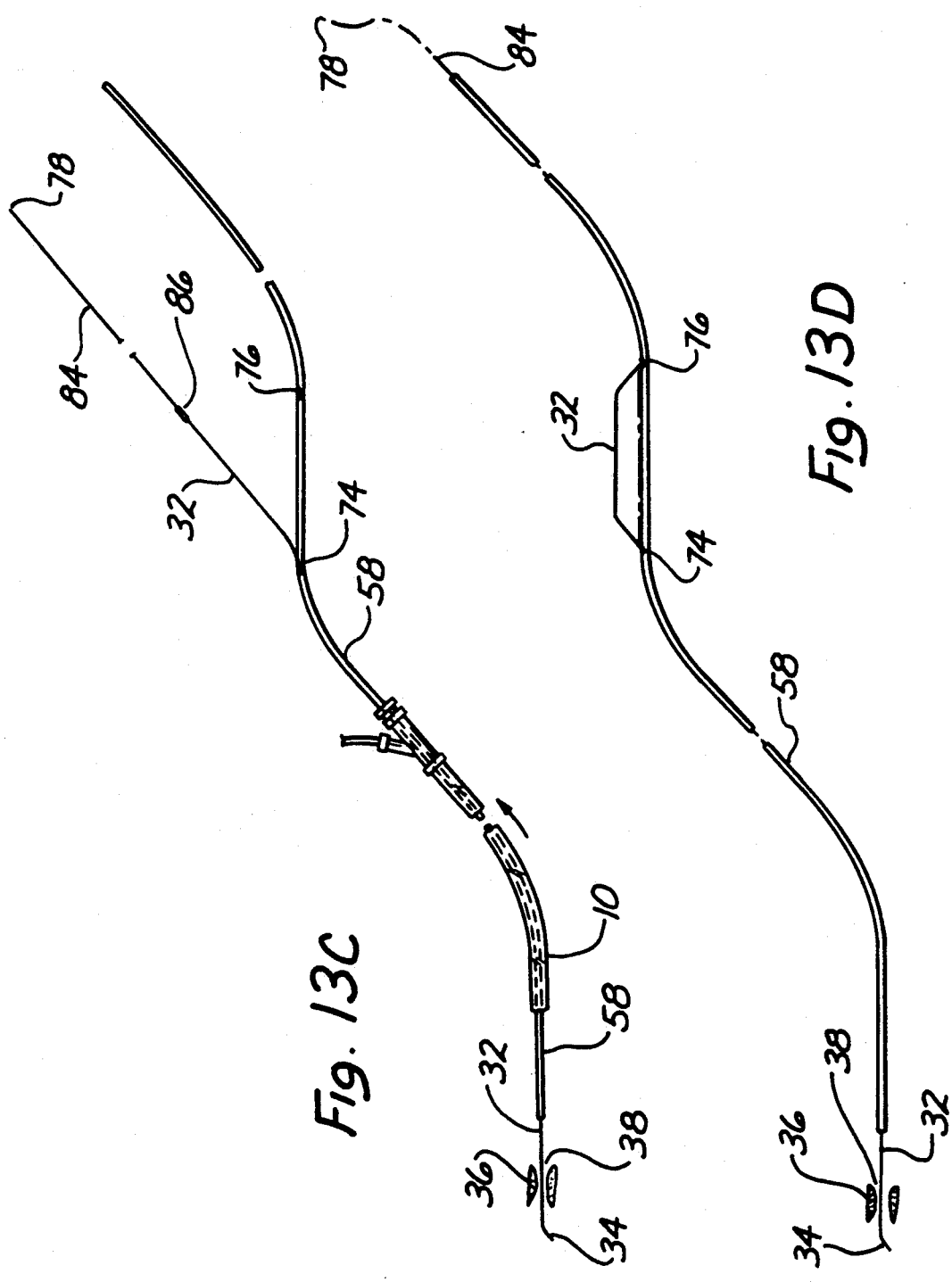

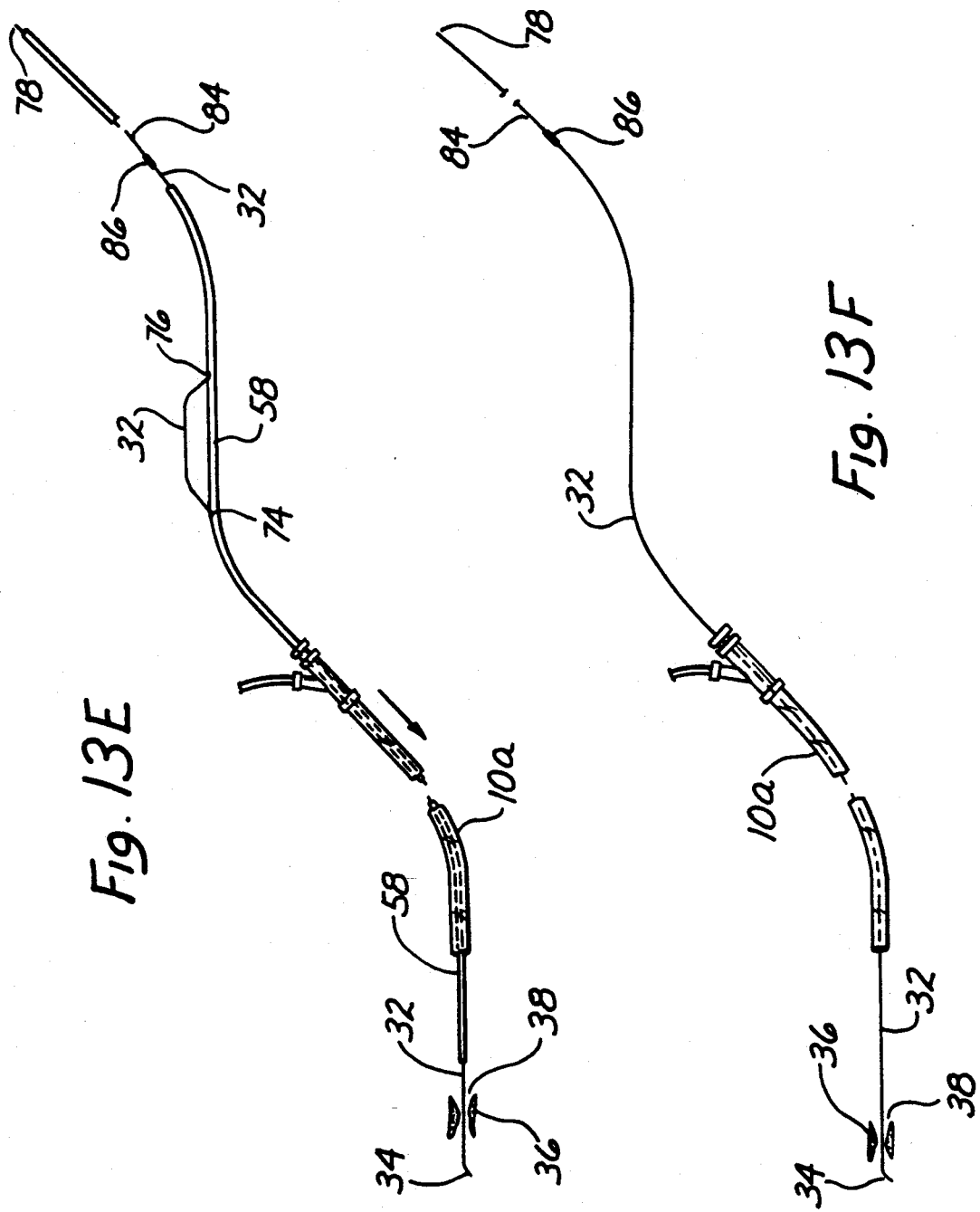

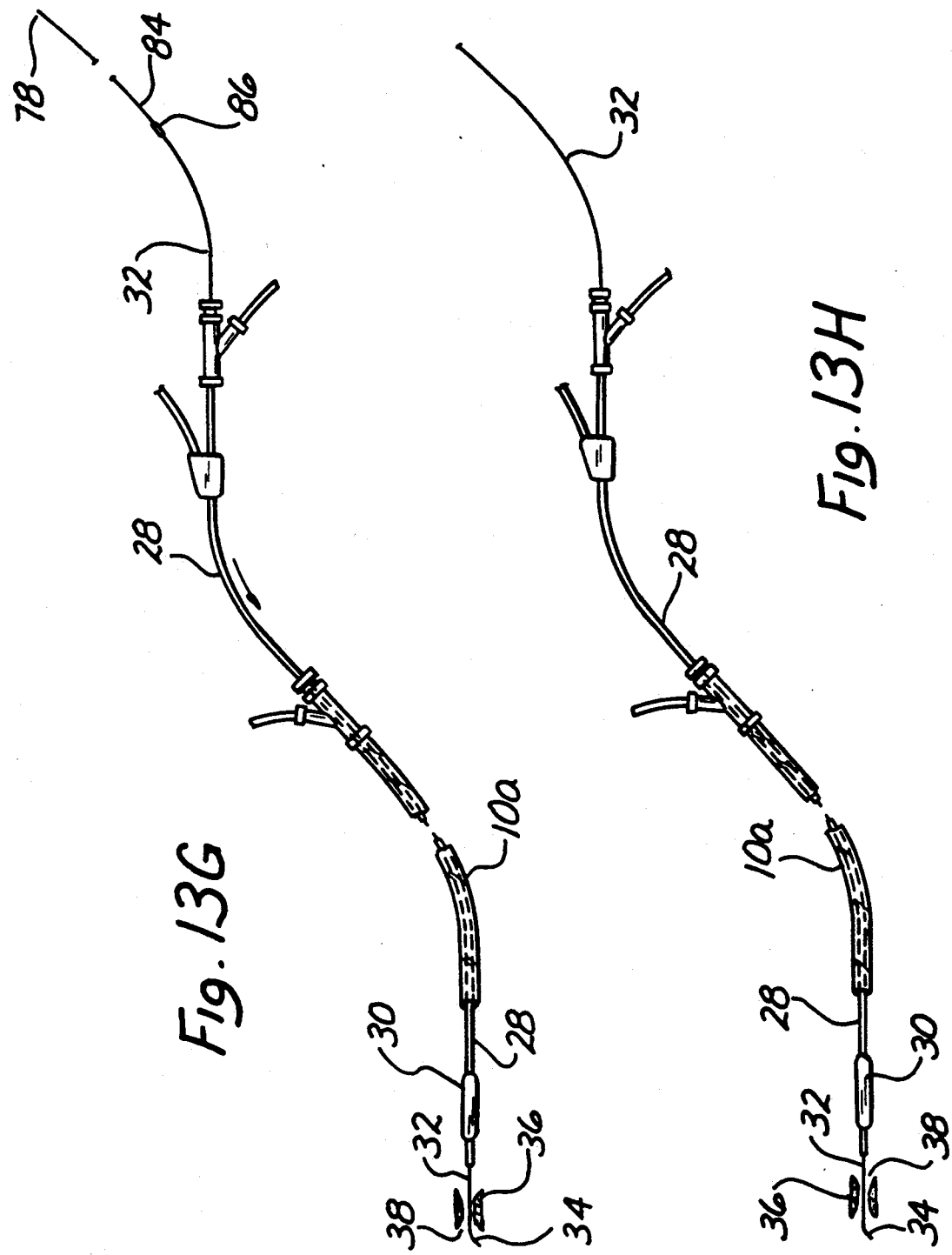

METHOD AND DEVICE FOR EXCHANGING CARDIOVASCULAR GUIDE CATHETER WHILE A PREVIOUSLY INSERTED ANGIOPLASTY GUIDE WIRE REMAINS IN PLACE

FIELD OF THE INVENTION

The present invention relates generally to medical equipment and more particularly to a method and device for removing a first cardiovascular guide catheter and replacing it with a second guide catheter while maintaining the operative position of a guide wire which has been previously inserted through the first guide catheter.

BACKGROUND OF THE INVENTION

Percutaneous transluminal angioplasty procedures have become commonly used in the treatment of various obstructive disorders of the human circulatory system. To date, angioplasty procedures have been utilized to treat stenotic lesions of the coronary arteries, iliac arterial obstructions, femoropopliteal arterial obstructions, renal arterial obstructions, cerebrovascular arterial obstructions, coarctations of the aorta, stenotic arteries in transplanted organs, stenotic saphenous vain bypass grafts, stenotic dialysis fistulas, stenotic portal systemic shunts and other obstructive vascular lesions.

In general, the usual technique for performing percutaneous transluminal angioplasty procedures requires the initial placement of an elongate flexible angiocatheter known as a "guide catheter". The guide catheter is initially inserted into an appropriate artery, such as the femoral artery or axillary artery, and subsequently advanced transluminally to a point where the distal tip of the guide catheter is positioned within a target blood vessel, near the obstructive lesion to be treated. A flexible guide wire is then inserted through the lumen of the guide catheter such that the distal end of the guide wire emerges out of and extends beyond the distal tip of the guide catheter. The guide wire is then advanced under fluoroscopic guidance, to a point whereat the distal end of the wire has advanced fully through the stenotic lesion or obstruction to be treated. After the distal end of the guide wire has been advanced through the stenotic lesion or obstruction, a small balloon catheter is then inserted and advanced over the guide wire, through the lumen of the guide catheter, to a point where the balloon of the balloon catheter lies adjacent the stenotic lesion or obstruction. Thereafter, the balloon is repeatedly inflated and deflated to bring about the desired dilation of the offending lesion and/or distention of the surrounding blood vessel wall. After such dilatory treatment is completed, the balloon catheter, guide wire and guide catheter are withdrawn and removed from the patient's body.

Various types and sizes of guide catheters are available. Care is generally taken, prior to the procedure, to pre-select a guide catheter of appropriate type and size for use in each particular patient. However, sometimes the pre-selected guide catheter proves to be inadequate and it becomes necessary or desirable to exchange one guide catheter for another during the course of the angioplasty procedure. If the decision to change a guide catheter is reached prior to insertion of the guide wire, the guide catheter may simply be extracted and replaced before the guide wire is inserted without any substantial risk of complication. However, if, as often occurs, the decision to replace the guide catheter is not reached until after the guide wire has already been fully inserted through the guide catheter and advanced through the stenotic lesion, any attempt to replace the guide catheter at that point is complicated by the need to maintain the previously inserted guide wire in its operative position, without accidentally pulling the guide wire back through the stenotic lesion.

In view of the foregoing problems in the prior art, there exists a need for a method and/or device to facilitate removal and replacement of a cardiovascular guide catheter while a flexible guide wire, which has been previously inserted through the lumen of the original guide catheter, remains in a substantially constant position without undue risk that the guide wire will be inadvertently pulled in a distal direction or otherwise pulled, retracted or jerked from its previously attained operative position.

The medical literature has previously reported two (2) techniques for removing an originally inserted guide catheter and replacing it with another guide catheter while maintaining the desired operative positioning of a previously inserted guide wire. One such technique is reported in: "Technique For Guiding Catheter Exchange During Coronary Angioplasty While Maintaining Guide Wire Access Across A Coronary Stenosis", by C. Mark Newton, M.D., Stephen A. Lewis, M.D., and George W. Vetrovec, M.D., *Catheterization and Cardiovascular Diaonosis*, 15:173-175 (1988). The first technique of Newton et al. requires the insertion of a relatively thick exchange wire be inserted and advanced through the lumen of the guiding catheter, beside the originally placed angioplasty guide wire. In particular, Newton et al. discloses the use of 0.35 inch diameter exchange wire which, when inserted through the lumen of the guiding catheter, lies adjacent to the existing angioplasty guide wire and provides necessary support during extraction and exchange of the guiding catheter. However, the passage of the exchange wire in immediate contact with the guide wire raises the possibility of inadvertent interference with and/or dislodgement of the guide wire. Moreover, the subsequent passage of the second guide catheter over the length of the existing guide wire and exchange wire may result in damage to or burring of the inner walls of the catheter.

The second technique for exchanging a guide catheter is described in "Guiding Catheter Exchanged During Coronary Angioplasty", by Stephen G. Warren, M.D., and J. Craig Barnett, M.D., *Catheterization and Cardiovascular Diagnosis*, 20:212-215 (1990). This second technique of Warren et al. is purely manipulative and relies solely upon the skill of the practitioner. The technique of Warren et al. requires placement of an extension wire on the proximal end of the original guide wire and, thereafter, the guiding catheter is slowly and carefully withdrawn while simultaneously forming a slackened area or "loop" in the guide wire within the ascending aorta. The slackened area or "loop" in the guide wire is formed to minimize the likelihood of inadvertent withdrawal of the distal end of the guide wire from its trans-stenotic position. After the first guide catheter has been withdrawn over the entire length of the extended guide wire, a second replacement guide catheter is then advanced over such extended guide wire and into a point where the distal end of the guide catheter is in the coronary ostium. Thereafter, the guide wire is gently retracted while the guide wire is simultaneously advanced through the ostium. By this procedure, the "loop" in the guide wire is eliminated and the new guide catheter takes its desired position within the coronary artery.

This second guide catheter replacement technique described by WARREN et al. is highly dependent upon the skill of the operator. Moreover, the technique described by WARREN et al. fails to provide any sort of enhanced support for the guide wire and, thus, allows the guide catheter to be moved over the thin guide wire without any protection or support for the guide wire.

One guide wire extension purported to facilitate exchange of a cardiovascular catheter with an existing guide wire in place is described in U.S. Pat. No. 4,917,103 (Gambale et al.). Another extendable guide wire for such procedures is described in U.S. Pat. No. 4,827,941 (Taylor et al.).

Other U.S. patents which purport to describe devices usable in exchanging cardiovascular catheters and/or guide wires are U.S. Pat. No. 4,927,413 (Hess) and U.S. Pat. No. 4,932,413 (Shockey et al.).

Because none of the prior art techniques or devices are truly optimal for effecting guide catheter exchange in all patients, there remains a need in the art for improved methods and/or devices for facilitating such guide catheter exchange without dislodging or disturbing the distal end positioning of a previously inserted guide wire.

SUMMARY OF THE INVENTION

The present invention overcomes some or all of the shortcomings of the prior art by providing a cardiovascular catheter exchange method and a cardiovascular "exchange catheter" device which facilitates removal of a first guide catheter and replacement thereof with a second guide catheter, without disturbing the operative placement of a guide wire which has previously been inserted through the lumen of the first guide catheter.

In accordance with the invention, there is provided a method of supporting and shielding a guide wire while removing and replacing a guide catheter through which said guide wire has been inserted, said method comprising the step of passing a tubular sheath member over the guide wire to protect and support the guide wire while the guide catheter is removed and replaced.

In accordance with a more specific aspect of the method of the present invention, there is provided a method for removing a first guide catheter and replacing said first guide catheter with a second guide catheter while maintaining the position of an elongate guide wire which has been previously been inserted through the first guide catheter, said method comprising the steps of:

(a) providing a flexible exchange catheter comprising a generally tubular body having an outer diameter which is smaller than the inner diameter of the first or second guide catheters, a proximal end, a distal end, at least one lumen extending longitudinally therethrough and a guide wire exit aperture formed in the generally tubular body between the proximal and distal ends thereof;

(b) passing the distal end of the exchange catheter onto the proximal end of the guide wire and advancing the exchange catheter over the guide wire in a distal direction to a point where the proximal end of the guide wire is adjacent the guide wire exit aperture of the exchange catheter;

(c) causing the proximal end of the guide wire to emerge from the lumen of the exchange catheter through the guide wire exit aperture;

(d) further advancing the exchange catheter over the guide wire in a distal direction to a point where the distal end of the exchange catheter is proximate the distal end of the first guide catheter;

(e) extracting the first guide catheter in a proximal direction over the exchange catheter and over guide wire and thereby removing said first guide catheter from the patient;

(f) advancing a second guide catheter in a distal direction over the exchange catheter and over the guide wire to a point where the second guide catheter has reached its desired operative position within the patient; and (g) proximally withdrawing and removing the exchange catheter, leaving the second guide catheter in its operative position with the guide wire extending therethrough.

Further in accordance with the method of the present invention, said method may further comprise the step of manual grasping, holding and manipulation of the portion of the guide wire which is emergent from the guide wire exit aperture, during at least portions of the time during which the original guide catheter, replacement guide catheter and/or exchange catheter device are being inserted and/or retracted. Such manual grasping, holding and/or manipulation of the guide wire enables the operator to maintain the desired operative placement of the distal end of the guide wire and serves to prevent the guide wire from becoming substantially displaced or distally retracted during the catheter exchange procedure. Additionally, the proximal end of the guide wire may be shielded within the body of the exchange catheter device when the first and second guide catheters are passed thereover so as to prevent damage to the lumens of the first or second guide catheters by the cut proximal end of the guide wire.

Further in accordance with the invention, there is provided an "exchange catheter" device comprising a flexible, generally tubular body having a proximal end, a distal end and at least one lumen extending longitudinally therethrough and at least one guide wire exit aperture formed therein between the proximal and distal ends thereof. An optional guide wire re-entry aperture may also be formed in the tubular body proximal to the guide wire exit aperture. A ramp member may be formed within the lumen of the tubular body to urge the leading tip of the guide wire out of the guide wire exit aperture as the exchange catheter is advanced over the guide wire.

The body of the exchange catheter device may be formed of any suitable material. Specifically, such exchange catheter device may be formed of tubular plastic, or, such exchange catheter device may be formed of an elongate coiled member such as a fine wire coiled about a hollow lumen to form a generally tubular sheath-like structure which may be passed over the outer surface of a guide wire.

Still further in accordance with the invention, there is provided a system for removing a first guide catheter and replacing it with a second guide catheter while a guide wire, previously inserted through the first guide catheter, remains in place. Such system comprises (a) a first guide catheter, (b) a second guide catheter, (c) an elongate guide wire and (d) a generally tubular exchange catheter. Additionally, the system of the present invention may further include (e) an extension wire attachable to the proximal end of the elongate guide wire to form a "guide wire assembly" which is sufficiently long such that the portion of the guide wire assembly which extends outside of the patient's body will be at least as long as the longest of said first and second guide catheters.

These, as well as other elements, objects and advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is an illustration of a prior art guide catheter inserted through the femoral artery of a human being in positioned for percutaneous transluminal angioplasty of the right coronary artery;

FIG. 2 is an enlarged cross-sectional view of the distal end of the prior art guide catheter of FIG. 1 disposed within the aortic arch;

FIG. 3 is an enlarged view of the tip of the prior art guide catheter of FIG. 2 showing the balloon catheter and guide wire extending therefrom with the guide wire extending through the lumen of the stenosis;

FIG. 4 is an illustration of the prior art percutaneous transluminal angioplasty system showing the guide catheter, balloon catheter, and guide wire;

FIG. 5 is an illustration of the prior art guide catheter, balloon catheter, and guide wire as an attempt is made to extend the balloon into the lumen of the stenosis, resulting in displacement of the tip of the guide catheter and deformation or bending of the balloon catheter;

FIG. 6 is an enlarged view of the tip of the prior art guide catheter, balloon catheter, and guide wire of FIG. 5;

FIG. 7 is a top plan view of the exchange catheter of the present invention;

FIG. 8 is an illustration of the exchange catheter of FIG. 7 after it has been inserted into the femoral artery of a human being and also showing the guide wire extending therefrom;

FIG. 9 is a sectional view of the exchange catheter of FIG. 7 showing the guide wire extending therefrom and re-inserted therein;

FIG. 10 is an enlarged cross-sectional view of the proximal end of the exchange catheter of FIG. 7 showing the position of the proximal end of the guide wire extension disposed therein such that a new guide catheter may be inserted over the exchange catheter without contacting the proximal end of the guide wire extension;

FIG. 11 is a cross-sectional side view of the first aperture of the exchange catheter of FIGS. 7 and 9;

FIG. 12 is a flow chart illustrating a preferred guide catheter exchange method of the present invention;

FIGS. 13A-13H illustrate the steps of FIG. 12 with corresponding letters indicating the illustration of corresponding steps.

DETAILED DESCRIPTION OF THE PREFERRED EMBODIMENT

The detailed description set forth below in connection with the appended drawings is intended to describe and illustrate a presently preferred embodiment of the invention, and is not intended to represent the only form in which the present invention may be constructed or utilized. The description provided herein sets forth the functions and sequence of steps for constructing and operating the invention in connection with the illustrated embodiment. It is to be understood, however, that the same or equivalent functions and sequences may be accomplished by different embodiments and it is intended that all such different embodiments be encompassed within the spirit and scope of the invention.

Broadly stated, the present invention comprises a flexible sheath-like member or "exchange catheter" which may be passed over the outer surface of a prepositioned guide wire to support and shield the guide wire while a surrounding guiding catheter is extracted and replaced. The preferred apparatus of the present invention incorporates specific elements and design attributes which enable the operator to carefully control and maintain the placement of the distal tip of the guide wire across a desired stenotic lesion, while the guide catheter is being exchanged, without undue risk of inadvertent disruption or movement of the guide wire tip back through the stenotic lesion. Also, the present invention includes a method for exchanging a coronary guide catheter wherein a protective sheath or "exchange catheter" of the above-described type is utilized.

The preferred apparatus and methodology described in the presently preferred embodiment is notably applicable to coronary angioplasty procedures and is specifically describe in such context. It is to be understood, however, that the apparatus and methodology of the present invention need not be limited to coronary artery procedure but, rather, may be utilized in a wide range of medical procedures wherein it is desirable to exchange one catheter for another while maintaining the operative location of a guide wire which has previously been inserted through a lumen of the original catheter.

FIGS. 1-6 set forth schematic diagrams of typical transluminal angioplasty procedures of the prior art and illustrations of problems which commonly occur during such procedures. The method and device of the present invention are illustrated in FIGS. 7-13H.

Referring now to FIG. 1, the path followed by a flexible guide catheter, balloon catheter, and guide wire during percutaneous transluminal coronary angioplasty is illustrated. The guide catheter 10 enters the human being 14 through an opening 12 to the femoral artery at the thigh and travels upward and into the heart. The proximal end 16 of the guide catheter 10 remains outside of the body and may be manipulated to effect motion of the distal end 18 within the heart. The guide wire and balloon catheter are inserted through the guide catheter 10 and thus follow the same path from the femoral artery to the heart.

Referring now to FIGS. 2 and 3, the position of the distal end 18 of the guide catheter 10 within the aortic arch 20 is illustrated. The tip 22 of the guide catheter 10 is disposed within the ostium 24 of the right coronary artery 26.

A balloon catheter 28 extends from the tip 22 of the guide catheter 10. A balloon 30 is disposed at the distal end of the balloon catheter 28. The balloon 30 is disposed within the right coronary artery 26 proximate a stenosis 36. The guide wire 32 extends through the lumen 38 of the stenosis 36.

Referring now to FIG. 4, a prior art flexible guiding catheter and balloon catheter system is illustrated. This prior art system comprises a flexible guide catheter 0 through which a guide wire 32 and/or balloon catheter 28 may be inserted to the site of stenosis 36. Once positioned at the site of the stenosis 36 the distal end 34 of the guide wire 32 is inserted through the lumen 38 of the stenosis 36 such that the balloon 30 may be urged over the guide wire 32 and through the lumen 38 of the stenosis 36 where it may be inflated to effect angioplasty.

Constant pressure ports 40 and 42 for the guide catheter 10 and the balloon catheter 28, respectively, provide for the introduction of saline solution or the like to prevent the backflow of blood through the catheters 10 and 28, and to facilitate flushing of the catheters after the introduction of dye, vasodilators, or the like. Syringes 44 and 46 permit the introduction through couplings 48 and 50, respectively, of dye, vasodilators, or the like into the guide catheter 10 and the balloon catheter 28. Trident housings 52 and 54 interconnect couplings 40 and 42 to the guide catheter 10 and the balloon catheter 28, respectively.

Referring now to FIGS. 5 and 6, occasionally difficulties are encountered when an attempt is made to insert the balloon 30 through the lumen 38 of a stenosis 36. If the lumen 38 of the stenosis 36 is so small that the balloon 30 must be forced therethrough, such forcing of the balloon catheter may cause the distal end 18 of the guide catheter 10 to be repelled or forced backwards away from the ostium 24 of the right coronary artery 26. The distal tip of the balloon catheter 28 may thus become substantially unsupported intermediate the balloon 30 and the distal end 18 of the guide catheter 10. The balloon catheter 28 may consequently form a deformation or bend 56 due to the lack of support. This prevents the balloon 30 from being forced further into the lumen 38 of the stenosis 36 since further urging of the balloon catheter 28 toward the stenosis 36 merely increases the amount of deformation or bend 56 instead of moving the balloon 30 through the stenosis 36.

A common prior art solution to this problem would have been to simply remove the original balloon catheter 28 and replace it with a second, more rigid, balloon catheter. Such replacement of the balloon catheter can be accomplished with minimal risk of disrupting positioning of the guide wire 32. Also, such replacement of balloon catheter With a more rigid balloon catheter will frequently overcome the problem as the more rigid balloon catheter would be less likely to deform or wrinkle 56 in its distal region where it remains unsupported by the guide catheter 10. However, such removal and replacement of the original balloon catheter is highly undesirable because balloon catheters are expensive disposable components which, once removed must be discarded and not reused. Furthermore, the substitution of a more rigid balloon catheter may not always achieve the desired result in view of the fact that the underlying problem of lack of support for the distal end of the balloon catheter remains unchecked. Accordingly, the procedure of removing and replacing the balloon catheter results in substantial added expense and sometimes fails to remedy the underlying problem.

In view of the expense and drawbacks associated with removal and replacement of the balloon catheter 28, it would be highly desirable if the operator could simply remove the originally inserted guide catheter and replace it with a different guide catheter having differing flexibility characteristics and/or configurational characteristics. Indeed, guide catheters are much cheaper than balloon catheters and, even if it were to be necessary to dispose of and not reuse the originally inserted guide catheter, such would still result in less expense than actual removal and replacement of the balloon catheter 28.

Therefore, a procedure for replacing the originally inserted or first guide catheter 10 with another guide catheter having different flexibility or configurational characteristics is desirable. However, any such procedure for replacing the originally inserted guide catheter 10 with another guide catheter must be carried out with continued control over the previously inserted guide wire 32 to ensure that the distal end of the guide wire 32 remains inserted through the stenosis 36. Indeed, if the guide wire 32 is inadvertently withdrawn from the stenosis, reinsertion of the guide wire may be rendered difficult or impossible. Therefore, once the guide wire 32 has been successfully inserted through the stenotic lesion, it is extremely desirable to maintain such positioning of the guide wire 32 until the PTCA procedure has been completed. In fact, the patient's life may well depend upon the ability to maintain the positioning of the guide wire within the lumen of the stenosis.

i. A Preferred Exchange Catheter Device

The presently preferred apparatus of the present invention comprises a pliable sheath member, referred to herein as an "exchange catheter" 58 which may be passed over or threaded over the outer surface of a flexible guide wire to shield and support the guide while a surrounding guide catheter is extracted and replaced.

As shown in FIGS. 7-11, a presently preferred sheath or exchange catheter 58 of the present invention comprises an elongate tubular catheter body 60 having a lumen 62 extending longitudinally therethrough. The catheter body 60 has an outer diameter which is smaller than the inner diameter of the original guide catheter 10, or the replacement guide catheter to be inserted. The distal end of the catheter body 60 is tapered and a flexible tubular tip member 70 is mounted on the distal end of the catheter body 60 forming an extension thereof such that the hollow lumen of the tubular tip member 70 is substantially continuous with the hollow lumen of the catheter body 60. A radiopaque band 72 is positioned between the distal end of the catheter body 60 and the flexible tip 70 so as to facilitate fluoroscopic visualization of the distal end of the exchange catheter 58.

A proximal guide wire exit aperture 74 is formed through the sidewall of the catheter body 60 near the approximate mid-point of the catheter body to permit a flexible guide wire 33 to pass from the inner lumen of the exchange catheter 58, outwardly through such guide wire exit aperture 74.

A plug 80 may be positioned in the lumen 62 of the catheter body 60 at a position immediately proximal to the guide wire exit aperture 74 so as to block the lumen 62 of the guide catheter 58 at that point. A ramp or sloped surface 82 may be formed on the distal aspect of the plug member 80 such that, as the exchange catheter 58 is advanced over the guide wire 32, the distal end of the guide wire 32 will register against ramp surface 82 and will be forced outwardly through guide wire exit aperture 74.

An optional guide wire re-entry aperture 76 may be formed proximal to the position of the guide wire exit aperture 74 to permit the proximal end of the guide wire 32 to be reinserted into the lumen 62 of the catheter body 60, thereby leaving a loop 33 of the guide wire 32 outside of the catheter body 60. Such loop 33 of the guide wire 32 may be directly grasped by the operator's hand, thereby allowing the operator to manipulate and hold the guide wire 32 in its desired position while the catheter exchange is taking place.

It will be appreciated that the second guide wire re-entry aperture 76 is optional and that the exchange catheter 58 could function with only a single guide wire exit aperture 74 formed therein. As shown in FIG. 8, when the proximal portion of the guide wire 32 extends out of the guide wire exit aperture 74, it may be directly grasped by the operator and guided/manipulated in the desired manner without the need for re-entering the proximal end of the guide wire 32 back into the lumen 62 of the exchange catheter 58.

An exchange catheter 58 of the present invention wherein the optional guide wire re-entry aperture 76 is provided, the ability to reinsert the proximal end of the guide wire through the guide wire re-entry aperture 76 and into the lumen of the guide catheter will provide the additional advantage of allowing the proximal end of the guide wire 32 to be housed within and shielded by the catheter body 60 while the initial guide catheter 10 is being withdrawn and while the new guide catheter 10 is subsequently being advanced thereover. This is desirable because the proximal ends of some guide wires may be sharp or may contain burrs which could cut or otherwise harm the inner lumen of the guide catheter 10 as it is passed over the proximal end of the guide wire 32. Thus, so long as the proximal end of the guide wire is positioned within the lumen 62 of the exchange catheter 58, the body of the exchange catheter will serve to shield and prevent the proximal end of the guide wire 32 from coming into contact with the inner luminal surface of either the original guide catheter 12 or the replacement guide catheter.

The length of the exchange catheter 58 and the locations of the exit aperture 74 and/or re-entry aperture 76 on the catheter 58 may be specifically selected to facilitate the desired function of the exchange catheter 58. For example, if the preferred exchange catheter 58 is sized for use in adult coronary artery angioplasty procedures, the overall length of the exchange catheter 58 is preferably approximately 290.4 centimeters, the catheter body 60 being approximately 290 centimeters in length and the distal tip 70 being approximately 0.4 centimeters in length. In the preferred embodiment shown, the length A from the proximal end 66 of the exchange catheter 58 to the optional guide wire re-entry aperture 76 is approximately 140 centimeters; the distance B between the re-entry aperture 76 and the exit aperture 74 is approximately 20 centimeters. The distance C between the guide wire exit aperture 74 and the proximal end of the tapered section 68 is approximately 129 centimeters; the length D of the tapered section 68 is approximately 1 centimeter and the length E of the flexible tip 70 is approximately 0.4 centimeters.

The inner and outer diameter of the preferred embodiment of the exchange catheter 58 is determined by the relative diameters of the guide wire 32 and the inner diameters of original and replacement guide catheters being used. To wit: the outer diameter of the exchange catheter, at its largest point, is slightly smaller than the inner diameter(s) of the guide catheters 10, 10a so as to allow the exchange catheter to pass easily through the lumens of the guide catheters 10, 10a. Also, the inner diameter of the exchange catheter is larger than the outer diameter of the guide wire to allow the exchange catheter to pass easily over the guide wire.

Generally, cardiovascular guiding catheters 10, 10a used in the art have inner luminals of constant diameter of about 0.072–0.078 inches. Flexible guide wires used in the art typically have constant outer diameters of about 0.010–0.018 inches. The exchange catheter device 58 of the present invention is preferably sized relative to the inner lumen size(s) of the guide catheters and the outer diameter of the guide wire being used in a particular procedure and, in view of the typical or standard guide catheter and guide wire sizes set forth above, may be specifically sized to be usable with such typical guide catheters and guide wire encountered in clinical or experimental practice.

In the presently preferred embodiment shown, the exchange catheter 58 of the present invention has an inner luminal diameter of approximately 0.020–0.023 inches and preferably about 0.021 inches (about 1.7 French) and an outer diameter of approximately 0.052–0.057 inches and preferably about 0.055 inches (about 4.3 French).

Optional markings or other visible indicia may be formed at various points on the catheter body 60 to permit the operator to visually determine how much of the exchange catheter 58 has been inserted into the patient's body at any given point in time. Also, optional markings or visual indicia may be formed around or near the exit aperture 74 and/or re-entry aperture 76 to assist the operator in easily seeing and locating such apertures.

In the preferred embodiment shown, the elongate catheter body 60 is formed of flexible nylon material commercially available as PEBAX P6 (Ato Chimie, Courbevoire, Hauts-De-Seine, France). PEBAX P6 has a Shore D durometer hardness of 65 and a flexural modulus (by the method of ASTMD-790) at 37° C. of approximately 30,000 psi. The soft distal tip 70 of the preferred embodiment shown is formed of PEBAX P3. PEBAX P3 has a Shore D durometer hardness of 35 and a flexural modulus (by the method of ASTMD-790) at 37° C. of approximately 5,000 psi.

Those skilled in the art will recognize that various other materials, other than the PEBAX materials disclosed above, may be utilized to form the catheter body 60 and distal tip 70 and that materials of varied hardness and flexural properties of such materials may be selected and utilized depending on the desired specific application of the exchange catheter 58.

One alternative is that, rather than forming the catheter body of a plastic tube, the catheter body may comprise an elongate strand, member or wire coiled about a generally hollow lumen to form a flexible, tube-like sheath or body having a hollow lumen extending therethrough.

The wire may be a metal wire.

Also, in some embodiments, a braided reinforcement member may be disposed in at least a portion of the tubular catheter body to reinforce that portion of the catheter body wherein said braided reinforcement member is disposed.

ii. A Preferred Catheter Exchange Method

As shown in FIG. 13A, an original guide catheter 10 is initially inserted into an artery (e.g. the femoral or axillary artery) and advanced to a desired operative position. A guide wire 32 is then inserted through the lumen of the original guide catheter 10 and advanced to a position where the distal end 34 of the guide wire 32 has penetrated or passed through the stenotic lesion 36 to be treated. A balloon dilation catheter 28 is then be advanced over the guide wire 32, through the lumen of the original guide catheter 10. An attempt is made to advance the balloon catheter 28 fully to a point where the dilation balloon 30 lies directly adjacent the stenotic lesion 36 to be treated. If it is found that the guide catheter 10 is not properly configured for the particular application or if it is found that the guide catheter 10 lacks sufficient rigidity to facilitate the desired placement of the balloon catheter 28, or if other problems with the guide catheter 10 are observed, a decision may be made to remove the original guide catheter 10 and to replace it with a substitute guide catheter 10a having a different configuration, different flexural properties or other differences relative to the original guide catheter 10.

After the decision has been made to remove and replace the original guide catheter 10, an extension wire 84 may be connected to the proximal end of the previously inserted guide wire 32 (see Step A in Flow diagram of FIG. 12) to form a long guide wire assembly which consists of both the original guide wire 32 and the extension wire 84. The extension guide wire 84 may be connected to the original guide wire 32 by way of a crimp connector 86 so as to form a substantially permanent connection therebetween. Alternatively, various screw connectors or other detachable connectors may be used to attach the extension guide wire 84 to the proximal end of the original guide wire 32.

Preferably, the length of the extension guide wire 84 is approximately equal to that of the original guide wire 32 such that, when the extension guide wire 84 is connected to the proximal end of the original guide wire 32, the guide wire assembly formed will be approximately twice the length of the original guide wire 32.

The length of the guide wire 32 or, alternatively, the combined length of the guide wire 32 and extension guide wire 84 (i.e. the length of the "guide wire assembly") is preferably such that, while the distal tip 34 of the guide wire remains in its desired operative position through the stenotic lesion 36, the portion of the guide wire assembly (the original guide wire 32 plus any guide wire extension 84) which extends outside of the human body is slightly longer than the overall length of either the original guide catheter 10 or the substitute guide catheter 10a.

Referring to FIG. 13B, after the extension guide wire 84 has been attached to the proximal end of the original guide wire 32, the balloon catheter 28 is then extracted in a proximal direction, over the guide wire assembly, and removed, thereby leaving just the original guide catheter 10 and the flexible guide wire 32 in place.

Thereafter, as shown in FIG. 13C, the proximal end 78 of the guide wire assembly is inserted into the distal end of an exchange catheter 58 and the exchange catheter 58 is advanced thereover in a distal direction. When the proximal end 78 of the guide wire assembly (e.g. the proximal end of the extension wire 84) reaches the guide wire exit aperture 74 of the exchange catheter 58, it is caused to pass outwardly through the guide wire exit aperture 74, as shown. The exchange catheter 58 is then further advanced over the guide wire 32 to a point where the distal tip of the exchange catheter 58 is positioned just proximal to the stenotic lesion 36. When so positioned, the exchange catheter 58 serves to sheath and surround the portion of the guide wire 32 that resides within the lumen of the original guide catheter 10.

After the exchange catheter 58 has been fully advanced to its desired location such that the distal end of the exchange catheter is just proximal to the stenotic lesion 36, the proximal end 78 of the guide wire assembly may be inserted into the optional guide wire re-entry aperture 76 as shown. The proximal end 78 of the guide wire assembly is then advanced in a proximal direction through the lumen of the exchange catheter 58 to a point where the proximal end 78 remains with the lumen of the exchange catheter 58 and a loop 33 of guide wire 32 protrudes outwardly from the body of the exchange catheter 58, between the guide wire exit aperture 74 and the guide wire re-entry aperture 76.

The loop 33 of guide wire extending between exit aperture 74 and re-entry aperture 76 may subsequently be drawn down tight against the outer surface of the exchange catheter 58 (as indicated by the phantom lines on FIG. 13D) by advancing the proximal end 78 of the guide wire assembly in a further proximal direction. When such maneuver is completed and the guide wire 32 is drawn down tight against the outer surface of the exchange catheter 58, the proximal end 78 of the guide wire assembly may extend out of and beyond the proximal end of the exchange catheter 58. Such extension of the proximal end 78 of the guide wire assembly is also shown in phantom lines on FIG. 13D.

With the loop 33 of guide wire 32 drawn down tightly against the region of the catheter body, the original guide catheter 10 is then withdrawn and pulled proximally over the body of the exchange catheter 58 and over the loop 33 of guide wire 32 which passes outside the exchange catheter 58, between apertures 74 and 76.

The original guide catheter 10 is initially withdrawn to a point where the distal tip of the guide catheter 10 is proximal to the guide wire re-entry aperture 76. During such withdrawal of the guide catheter 0, the operator may maintain manual control of the guide wire assembly by grasping the proximal end of the guide wire assembly as it extends out of the proximal end of the exchange catheter.

With the original guide catheter 10 withdrawn to a point where its distal tip lies proximal to the re-entry aperture 76, the guide wire 32 is grasped by the operator and pulled in a manner which causes the proximal end 78 of the guide Wire assembly to once again retract into the proximal end of the exchange catheter, thereby recreating the bulbous slackened loop 33 of guide wire 32 between the exit aperture 74 and re-entry aperture 76. Such maneuver also causes the distal tip 78 of the guide wire to become fully housed within the lumen of the exchange catheter 58. At that point, the original guide catheter 10 is further retracted in a proximal direction the rest of the way off of the surface of the exchange catheter 58 and without direct contact with the proximal end 78 of the guide wire assembly as such proximal end 78 is housed within the lumen of the exchange catheter 58.

The open distal end of second guide catheter 10a is then advanced over the proximal end of the exchange catheter 58 and the second guide catheter 10a is advanced to a point where the distal tip of the second guide catheter 10a lies just proximal to the guide wire re-entry aperture 76. At that point, the bulbous loop 33 of guide wire 32 between exit aperture 74 and re-entry aperture 76 is once again flattened or pressed down tight against the body of the catheter 58 in a manner which causes the proximal end 78 of the guide wire assembly to once again extend out of the proximal end of the exchange catheter 58.

Thereafter, the replacement guide catheter 10a is further advanced in a distal direction over the surface of the guide catheter 58 and over the flattened loop 33, to a point where the distal tip of the replacement guide catheter 10a assumes a desired operative location (e.g. inserted within the ostium of the coronary artery wherein the stenotic lesion 36 is located). During such advancement of the catheter, the operator may manually control the position of the guide wire 32 by grasping and/or manipulating the proximal end 78 of the guide wire assembly as it extends out of and beyond the proximal end of the exchange catheter 58.

After the replacement guide catheter 10a has been fully advanced to its desired operative position, the flattened loop 33 of guide wire 32 between the guide wire exit aperture 74 and guide wire re-entry aperture 76 is once again be grasped and pulled outwardly from the catheter in a manner which causes the proximal end 78 of the guide wire assembly to be once again drawn into the proximal portion of the exchange catheter 58 and whereby the loop 33 once again becomes bulbous or slackened such that the operator may manually grasp such loop 33 in order to maintain manual control of and to manipulate the guide wire 32 as the exchange catheter is slowly withdrawn the rest of the way off of the guide wire assembly.

As shown in FIG. 13F, after the exchange catheter 58 has been fully withdrawn of the guide wire assembly and with the second guide catheter 10a situated in its desired operative position, the original guide wire 32 has at all times been maintained in its original operative position such that its distal end remains inserted through the stenotic lesion 36 to be treated.

As shown in FIG. 13H, after the guide catheter exchange procedure has been completed, the extension wire 84 may optionally be removed from the proximal end of the original guide wire 32, leaving only the original guide wire 32 in place for subsequent operation.

Having thus completed the guide catheter exchange, the operator may once again advance the balloon catheter 28 over the guide wire 32 and through the newly inserted second guide catheter 10a to effect the desired dilation of the stenotic lesion 36.

The foregoing detailed description and the accompanying drawings are provided for the purpose of describing and illustrating presently preferred embodiments of the invention. It is to be understood that the invention is not limited to the preferred embodiments specifically described herein, but is capable of numerous rearrangements, modifications and substitutions without departing from the spirit of the invention. It is intended that all such rearrangements, modifications and substitutions be included within the scope of the following claims.

What is claimed is:

1. A method for removing a first guide catheter and replacing said first guide catheter with a second guide catheter while maintaining the position of an elongate guide wire which has previously been inserted through the first guide catheter, said method comprising the steps of:
   (a) providing a flexible exchange catheter comprising a generally tubular body having an outer diameter which is smaller than the inner diameter of the first or second guide catheters, a proximal end, a distal end, at least one lumen extending longitudinally therethrough and a guide wire exit aperture formed in the generally tubular body between the proximal and distal ends thereof;
   (b) passing the distal end of the exchange catheter onto the proximal end of the guide wire and advancing the exchange catheter over the guide wire in a distal direction to a point where the proximal end of the guide wire is adjacent the guide wire exit aperture of the exchange catheter;
   (c) causing the proximal end of the guide wire to emerge from the lumen of the exchange catheter through the guide wire exit aperture;
   (d) further advancing the exchange catheter over the guide wire in a distal direction to a point where the distal end of the exchange catheter is proximate the distal end of the first guide catheter;
   (e) extracting the first guide catheter in a proximal direction over the exchange catheter and over guide wire and thereby removing said first guide catheter from the patient;
   (f) advancing a second guide catheter in a distal direction over the exchange catheter and over the guide wire to a point where the second guide catheter has reached its desired operative position within the patient;
   (g) proximally withdrawing and removing the exchange catheter, leaving the second guide catheter in its operative position with the guide wire extending therethrough.

2. The method of claim 1 further comprising the step of:
   grasping and holding the portion of the guide wire which is emergent from the guide wire exit aperture and exerting force upon said guide wire to prevent said guide wire from becoming substantially displaced during further advancement of the exchange catheter over the guide wire.

3. The method of claim 1 further comprising the step of:
   grasping and holding the portion of the guide wire which is emergent from the guide wire exit aperture and exerting force upon said guide wire to prevent said guide wire from becoming substantially displaced during extraction of the first guide catheter in a proximal direction.

4. The method of claim 1 further comprising the step of:
   grasping and holding the portion of the guide wire which is emergent from the guide wire exit aperture and exerting force upon said guide wire to prevent said guide wire from becoming substantially displaced during placement of the second guide catheter in a distal direction.

5. The method of claim 1 further comprising the step of:
   grasping and holding the portion of the guide wire which is emergent from the guide wire exit aperture and exerting force upon said guide wire to prevent said guide wire from becoming substantially displaced during withdrawal and removal of the exchange catheter.

6. The method of claim 1 wherein
   the exchange catheter further comprises a guide wire re-entry aperture formed proximal to said guide wire exit aperture;
and wherein, between steps (c) and (d), the method further comprises the additional step of:
   inserting the proximal end of the guide wire into the guide wire re-entry aperture and further advancing the proximal end of the guide wire in a proximal direction through the lumen of the exchange catheter such that a loop of guide wire remains outside of the exchange catheter between said guide wire exit aperture and said guide wire re-entry aperture.

7. A method of supporting and shielding a guide wire while removing and replacing a guide catheter through which said guide wire has been inserted, said method comprising the step of:

passing a tubular sheath member over the guide wire to protect and support the guide wire while the guide catheter is removed and replaced.

8. The method of claim 7 further comprising the step of:

attaching an extension wire to the guide wire to form a guide wire assembly having an extracorporeal portion which is at least as long as the longest guide catheter to be removed or inserted.

9. A method of supporting and shielding a guide wire while removing and replacing a guide catheter through which said guide wire has been inserted, said method comprising the steps of:

providing a tubular sheath member having a proximal end, a distal end and a guide wire exit aperture formed therein between the proximal and distal ends thereof;

passing the distal end of the tubular sheath over the guide wire and advancing the tubular sheath in a distal direction to a point where the proximal end of the guide wire is adjacent the guide wire exit aperture;

causing the proximal end of the guide wire to emerge out of the guide wire exit aperture;

further advancing the tubular sheath member to a point where the tubular sheath member extends through the lumen of the guide catheter;

withdrawing and removing the original guide catheter;

passing a replacement guide catheter over the guide wire and tubular sheath member and advancing said replacement guide catheter in a distal direction to a fully inserted operative position; and withdrawing the tubular sheath member in a distal direction and removing the tubular sheath member to leave the replacement guide catheter in place with the guide wire inserted therethrough.

10. The method of claim 9 further comprising the step of:

grasping and exerting force on the portion of the guide wire which is emergent from the guide wire exit aperture to maintain the position of the guide wire while the tubular sheath, the guide catheter and replacement guide catheter are individually advanced and withdrawn.

11. An exchange catheter for use in combination with an elongate guide wire, comprising:

a flexible generally tubular body having a proximal end, a distal end, and at lest one lumen extending longitudinally therethrough;

an elongate guide wire extending through the lumen of the tubular body, the guide wire having a distal end and a proximal end;

at least one guide wire exit aperture formed in the tubular body portion between the proximal and distal ends thereof, the proximal end of the guide wire extending from the lumen outwardly through the exit aperture; and a guide wire re-entry aperture formed in the generally tubular body proximal to said guide wire exit aperture, the proximal end of the guide wire reinserted into the lumen through the re-entry aperture such that a loop of guide wire remains outside the exchange catheter between the exit aperture and the re-entry aperture.

12. The exchange catheter of claim 11 further comprising:

a tapered portion formed at the distal end of said tubular body.

13. The exchange catheter of claim 12 further comprising:

a flexible tip formed on and extending distally from said tapered portion, said flexible tip being comprised of softer material than said tubular body.

14. The exchange catheter of claim 13 wherein said exchange catheter body comprises a flexible plastic tube formed of PEBAX P6 material and said flexible tip member comprises a tubular tip formed of PEBAX P3 material.

15. The exchange catheter of claim 11 further comprising a flexible tip formed on the distal end of the generally tubular body, said flexible tip being more flexible than said tubular body.

16. The exchange catheter of claim 15 wherein said exchange catheter body comprises a flexible plastic tube formed of PEBAX P6 material and said flexible tip member comprises a tubular tip formed of PEBAX P3 material.

17. The exchange catheter of claim 15 wherein said tubular body is approximately 290 centimeters in length and said flexible distal tip is approximately 0.4 centimeters in length.

18. The exchange catheter of claim 11 further comprising:

a radiopaque marking member disposed on the tubular body to facilitate radiographic visualization of the exchange catheter.

19. The exchange catheter of claim 18 wherein said exchange catheter further comprises a flexible plastic tube formed of PEBAX P6 material.

20. The exchange catheter of claim 11 wherein said generally tubular body comprises a flexible plastic tube.

21. The exchange catheter of claim 11 wherein said exchange catheter body comprises an elongate member coiled about a hollow inner lumen to form said generally tubular body.

22. The exchange catheter of claim 21 wherein said elongate member comprises a metal wire coiled about a hollow inner lumen.

23. The exchange catheter of claim 11 further comprises a braided reinforcement member disposed in at least a portion of said tubular body.

24. The exchange catheter of claim 11 wherein said exchange catheter is approximately 290 centimeters in length.

25. The exchange catheter of claim 11 wherein the distance from the proximal end of the exchange catheter to the guide wire exit aperture is approximately 160 centimeters and the distance from the guide wire exit aperture to the distal tip of the exchange catheter is approximately 130.4 centimeters.

26. The exchange catheter of claim 11 wherein the distance from the proximal end of the exchange catheter to the guide wire re-entry aperture is approximately 140 centimeters, the distance from the guide wire re-entry aperture to the guide wire exit aperture is approximately 20 centimeters and the distance from the guide wire exit aperture to the distal tip of the exchange catheter is approximately 130.4 centimeters.

27. The exchange catheter of claim 11 wherein the lumen of the exchange catheter has a diameter of approximately 0.020–0.023 inches and wherein the outer diameter of the exchange catheter is approximately 0.052–0.057 inches.

28. The exchange catheter of claim 11 wherein the inner diameter of the exchange catheter lumen is about 0.021 inches and the outer diameter of the exchange catheter is about 0.055 inches.

29. An exchange catheter according to claim 11, wherein said guide wire exit aperture is formed in the tubular body at about the mid-point between the proximal and distal ends thereof.

30. An exchange catheter comprising:
 a flexible generally tubular body having a proximal end, a distal end, and at least one lumen extending longitudinally therethrough;
 at least one guide wire exit aperture formed in the tubular body portion between the proximal and distal ends thereof;
 a guide wire re-entry aperture formed in the generally tubular body proximal to said guide wire exit aperture; and
 a ramp member formed within the lumen of the tubular body adjacent the guide wire exit aperture to engage the leading tip of a guide wire being advanced in a proximal direction through the lumen and to cause the proximal end of the guide wire to pass out of said guide wire exit aperture.

31. The exchange catheter of claim 30 further comprising a tapered portion formed at the distal end of said tubular body.

32. The exchange catheter of claim 31 further comprising a flexible tip formed on and extending distally from said tapered portion, said flexible tip being comprised of softer material than said tubular body.

33. The exchange catheter of claim 32 wherein said exchange catheter comprises a flexible plastic tube formed of PEBAX P6 material and said flexible tip member comprises a tubular tip formed of PEBAX P3 material.

34. The exchange catheter of claim 30 further comprising a flexible tip formed on the distal end of the generally tubular body, said flexible tip being more flexible than said tubular body.

35. The exchange catheter of claim 34 wherein said exchange catheter comprises a flexible plastic tube formed of PEBAX P6 material and said flexible tip member comprises a tubular tip formed of PEBAX P3 material.

36. The exchange catheter of claim 34 wherein said tubular body is approximately 290 centimeters in length and said flexible distal tip is approximately 0.4 centimeters in length.

37. The exchange catheter of claim 30 further comprising a radiopaque marking member disposed on the tubular body to facilitate radiographic visualization of the exchange catheter.

38. The exchange catheter of claim 37 wherein said exchange catheter further comprises a flexible plastic tube formed of PEBAX P6 material.

39. The exchange catheter of claim 30 wherein said generally tubular body comprises a flexible plastic tube.

40. The exchange catheter of claim 30 wherein said exchange catheter body comprises an elongate member coiled about a hollow inner lumen to form said generally tubular body.

41. The exchange catheter of claim 40 wherein said elongate member comprises a metal wire coiled about a hollow inner lumen.

42. The exchange catheter of claim 30 further comprising a braided reinforcement member disposed in at least a portion of said tubular body.

43. The exchange catheter of claim 30 wherein said exchange catheter is approximately 290 centimeters in length.

44. The exchange catheter of claim 30 wherein the distance from the proximal end of the exchange catheter to the guide wire exit aperture is approximately 160 centimeters and the distance from the guide wire exit aperture to the distal tip of the exchange catheter is approximately 130.4 centimeters.

45. The exchange catheter of claim 30 wherein the distance from the proximal end of the exchange catheter to the guide wire re-entry aperture is approximately 140 centimeters, the distance from the guide wire re-entry aperture to the guide wire exit aperture is approximately 20 centimeters and the distance from the guide wire exit aperture to the distal tip of the exchange catheter is approximately 130.4 centimeters.

46. The exchange catheter of claim 30 wherein the lumen of the exchange catheter has a diameter of approximately 0.020–0.023 inches and wherein the outer diameter of the exchange catheter is approximately 0.052 to 0.057 inches.

47. The exchange catheter of claim 30 wherein the inner diameter of the exchange catheter lumen is about 0.021 inches and the outer diameter of the exchange catheter is about 0.055 inches.

48. The exchange catheter of claim 30 wherein said guide wire exit aperture is formed in the tubular body at about the mid-point between the proximal and distal ends thereof.

49. A system for removing a first guide catheter or replacing said first guide catheter with a second guide catheter while a guide wire, previously inserted through the first guide catheter, remains in place, said system comprising:
 a first guide catheter having a proximal end, a distal end, an outer surface and a lumen extending longitudinally therethrough, said outer surface being of a first outer diameter at its largest point and said lumen being of a first inner diameter at its narrowest point;
 a second guide catheter having a proximal end, a distal end, an outer surface and a lumen extending longitudinally therethrough, said outer surface being of a second outer diameter at its largest point and said lumen being of a second inner diameter at its narrowest point;
 an elongate guide wire having a proximal end and a distal end, said guide wire having, at its largest point, an outer diameter which is smaller than either the first inner diameter of the first guide catheter or the second inner diameter of the second guide catheter so that the guide wire may pass through and reside within the lumens of the first and second guide catheters; and
 a generally tubular exchange catheter having a proximal end, a distal end, an outer surface, a lumen extending longitudinally therethrough and guide wire exit aperture formed therein between the proximal and distal ends thereof, said exchange catheter having: (a) an outer diameter which is smaller than the first and second inner diameters of the first and second guide catheters and (b) an inner diameter which is larger than the outer diameter of the elongate guide wire.

50. The system of claim 49 further comprising:
an extension wire attachable to the proximal end of the elongate guide wire to form a guide wire assembly which, when fully inserted through the guide catheter, will have an exteriorized portion of a length at least equal to the longest of said first and second guide catheters.

51. The system of claim 49 wherein said exchange catheter further comprises:
a guide wire re-entry aperture formed proximal to said guide wire exit aperture.

52. The system of claim 49 wherein the inner diameters of the first and second guide catheters are equal.

53. The system of claim 49 wherein the inner diameters of the first and second guide catheters are different and the outer diameter of the exchange catheter is smaller than the smallest of the inner diameters of said first and second guide catheters.

* * * * *